(12) United States Patent
Keefe et al.

(10) Patent No.: US 9,058,435 B2
(45) Date of Patent: Jun. 16, 2015

(54) LABELING METHOD AND APPARATUS FOR DOCUMENTING THE OCCURRENCE OF TRIGGERING EVENTS

(76) Inventors: Gary Keefe, Brecksville, OH (US); Alan Gilbert, Hudson, OH (US)

( * ) Notice: Subject to any disclaimer, the term of this patent is extended or adjusted under 35 U.S.C. 154(b) by 51 days.

(21) Appl. No.: 13/494,213

(22) Filed: Jun. 12, 2012

(65) Prior Publication Data

US 2013/0327822 A1     Dec. 12, 2013

(51) Int. Cl.
*G06K 15/00* (2006.01)
*G06F 17/40* (2006.01)
*G06F 19/00* (2011.01)

(52) U.S. Cl.
CPC ............... *G06F 17/40* (2013.01); *G06F 19/30* (2013.01)

(58) Field of Classification Search
CPC .......................... G06F 19/3462; G06Q 50/22
USPC .................... 235/375, 383; 705/2; 53/411
See application file for complete search history.

(56) References Cited

U.S. PATENT DOCUMENTS

| | | | | |
|---|---|---|---|---|
| 6,155,485 | A * | 12/2000 | Coughlin et al. | 235/383 |
| 6,170,746 | B1 * | 1/2001 | Brook et al. | 235/385 |
| 7,016,752 | B1 * | 3/2006 | Ruben et al. | 700/117 |

\* cited by examiner

*Primary Examiner* — Jamara Franklin
(74) *Attorney, Agent, or Firm* — Pearne & Gordon LLP

(57) ABSTRACT

Provided is a labeling apparatus that generates a label for labeling a drug container. The labeling apparatus includes a code reader that interrogates a computer-readable code, and a local computer-readable memory that stores a drug formulary with a plurality of drug entries. A processing component identifies, from the formulary, a specific drug that corresponds to the computer-readable code read by the code reader and creates log entries in response to triggering events. The log entries include at least one of system information, user information, drug information, and patient information. And a printer is provided to print label content identifying the specific drug onto a label that is to be applied to the drug container.

12 Claims, 6 Drawing Sheets

LABELING METHOD AND APPARATUS FOR DOCUMENTING THE OCCURRENCE OF TRIGGERING EVENTS

BACKGROUND OF THE INVENTION

1. Field of the Invention

This application relates generally to a labeling apparatus for generating labels and, more particularly, to a labeling apparatus that records a history of activities relating to the use of the labeling apparatus.

2. Description of Related Art

Conventional labeling systems typical receive instructions to generate label content that is to be printed on labels. When used in certain fields such as the medical field, for example, the accuracy of the label content is important. Erroneous label content can introduce delays in the provision of healthcare to patients, requiring clinicians to resolve any inaccuracies before tending to the needs of patients.

Further, the label content may be required to comply with industry standards that are universally applicable to different healthcare providers as well as internal procedures mandated by individual healthcare providers. Generating labels with label content that deviates from the industry standards and/or internal mandates can introduce confusion to patient care. The entire medical staff can be trained to comply with the industry standards and internal mandates, but there may be labeling scenarios where the standards and mandates are silent. Individual staff members may also misunderstand or overlook what is required by the standards and mandates, and there may be instances where it is necessary to override an internal mandate to generate a label. Traditional labeling systems have thus far required laborious documentation procedures to document the generation of each label to identify when generated labels fail to comply with an industry standard or an internal mandate.

BRIEF SUMMARY OF THE INVENTION

Accordingly, there is a need in the art for a method and labeling apparatus that records historical events involving the labeling apparatus to identify at least one of user information, system information, and labeling information relating to such historical events.

According to one aspect, the subject application involves a labeling apparatus that generates a label for labeling a drug container. The labeling apparatus includes a code reader that interrogates a computer-readable code, and a local computer-readable memory that stores a drug formulary with a plurality of drug entries. A processing component identifies, from the formulary, a specific drug that corresponds to the computer-readable code read by the code reader and creates log entries in response to triggering events. The log entries include at least one of system information, user information, drug information, and patient information. And a printer is provided to print label content identifying the specific drug onto a label that is to be applied to the drug container.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
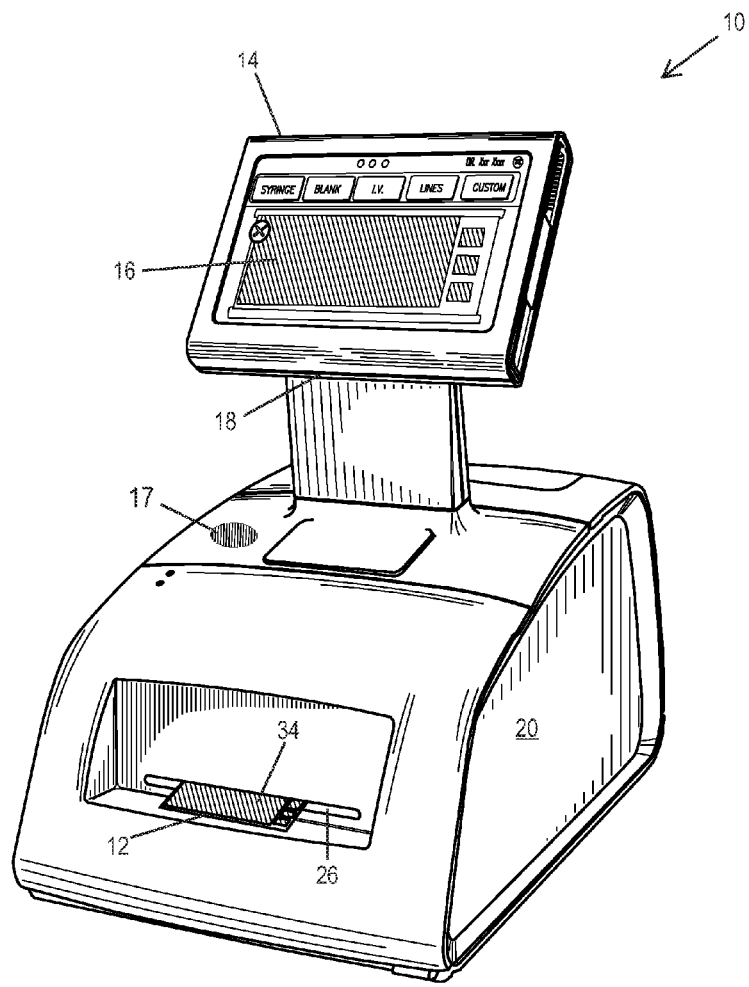
FIG. 1 shows an illustrative embodiment of a labeling apparatus for generating labels to be applied to medicinal substances in a medical facility.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

FIG. 1 shows an illustrative embodiment of a labeling apparatus, referred to herein as a computer terminal 10, that includes a touch-screen display 14 pivotally coupled to a cabinet 20 for displaying a virtual label 16 comprising a computer-generated preview of the label content 34 that will be printed onto a label 12, which can be applied to a container that stores a medicinal substance. An example of such a computer terminal is described in U.S. patent application Ser. No. 12/901,110, which is incorporated by reference herein in its entirety. The display 14 can also optionally display soft keys that, when touched by a technician or any other user, inputs data and commands to be received by the computer terminal 10.

Although described herein as being a stand-alone, monolithic unit with integrated scanner 18, printer 26 and display 14 as described in detail below, the computer terminal 10 can optionally be implemented as a distributed system. As a distributed system, the computer terminal 10 can include a processing component such as a computer tower case enclosing internal computer processing components operatively connected via a hard-wired or wireless connection to a peripheral, hand-held embodiment of the scanner, for example. Likewise, the distributed system can include a peripheral embodiment of the printer operatively connected to receive the label content from the computer tower case and print the physical label via a hard-wired or wireless connection.

The virtual label 16 is a computer-generated rendering of the label 12 that offers the user visual confirmation of the appearance of the physical label 12 to be printed by a printer 26. A computer-input peripheral such as a non-contact scanner 18 can be provided at a convenient location, such as integrally formed in a bottom portion of the display 14 to read a machine-readable code supported beneath the scanner 18 for example. Integrally forming the scanner 18 as part of the display 14 provides for space savings over an arrangement where the scanner 18 is formed as a separate peripheral, which can be repositioned relative to the display 14. However, other embodiments can allow for a separate and distinct scanner 18 and/or display 14.

The computer-input peripheral can be a barcode reader or radio-frequency identification ("RFID") tag reader, or any other device that reads a machine-readable code such as a barcode or RFID code, respectively, or any other machine-readable code without requiring physical contact between the computer terminal and the code, and optionally the user during entry of the code. According to alternate embodiments, the display 14 can be utilized by a user as the computer-input peripheral. For such embodiments, the soft keys displayed by the display 14 can be selected to input information such as a medicinal substance being prepared to be administered to a patient or other information to be utilized in generating the label as described herein. According to yet alternate embodiments, a speaker 17 can optionally be provided to the display 14, to a display mounting arm supporting the display 14, or any other portion of the computer terminal 10 to broadcast audible sounds.

Figure 2:
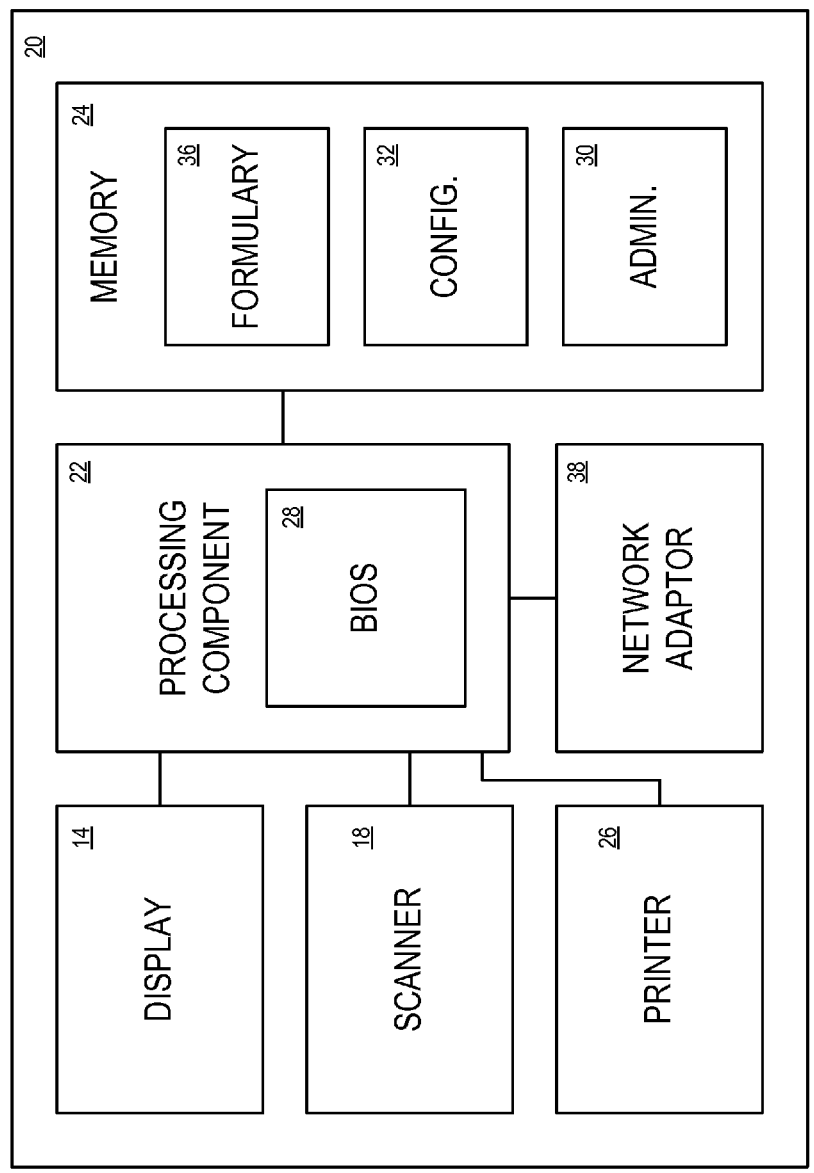
FIG. 2 shows a block diagram schematically depicting components of a labeling apparatus for generating labels to be applied to medicinal substances in a medical facility.

The computer terminal 10 also includes the cabinet 20 that houses or supports components that are operable to produce the label 12 in compliance with a medical labeling standard. But if what is being labeled is anything other than the medicinal substance, then the label 12 produced is to be compliant with a standard developed by a trade or professional organization, governing body, government agency, a healthcare provider or facility such as a hospital, or any other standards body setting forth policies for labeling such material. The label 12 can also optionally be required to be generated according to an internally-mandated work flow, described in detail below, established by the healthcare facility where the computer terminal 10 is located for use. The internal components housed within the cabinet 20 are schematically illustrated by the block diagram of FIG. 2. The components can be formed from an arrangement of computer hardware such as ASICs, computer processors, programmable logic controllers and other circuitry; or a combination of computer hardware and computer-executable instructions. For example, a processing component 22 is provided to execute computer-executable instructions stored in a non-transitory, computer-readable memory 24 such as a hard disk drive, read-only memory ("ROM"), random access memory ("RAM"), optical disc, or any other suitable memory device, or any combination thereof. The computer-executed instructions, when executed by the computer processor 22, result in the performance of the method of generating a label for a medicinal substance described in detail below.

A BIOS 28 is provided to load the operating system and other such administrative instructions 30 stored in the memory 24 and manage hardware interface permissions of the computer terminal 10. The operating system can be configured to only load authorized updates to prevent unauthorized changes to the formulary 36, configuration data 32 and administration instructions 30. Configuration data 32 controls various features of the computer terminal 10 that are active and available for use at any given time. The configuration data 32 can optionally be stored, updated and deleted from the memory 24 by the introduction of a so-called smart drive comprising a USB compatible flash memory to the computer terminal 10. When the smart drive is introduced to the computer terminal 10, it establishes the configuration data 32 of the computer terminal 10. The configuration data 32 can optionally be used to deactivate functional features that the computer terminal 10 would otherwise be able to perform based on the model of the computer terminal 10 purchased. Accordingly, a common hardware platform of the computer terminal 10 can be configured in a plurality of different functional configurations based on the configuration data 32.

Figure 3:
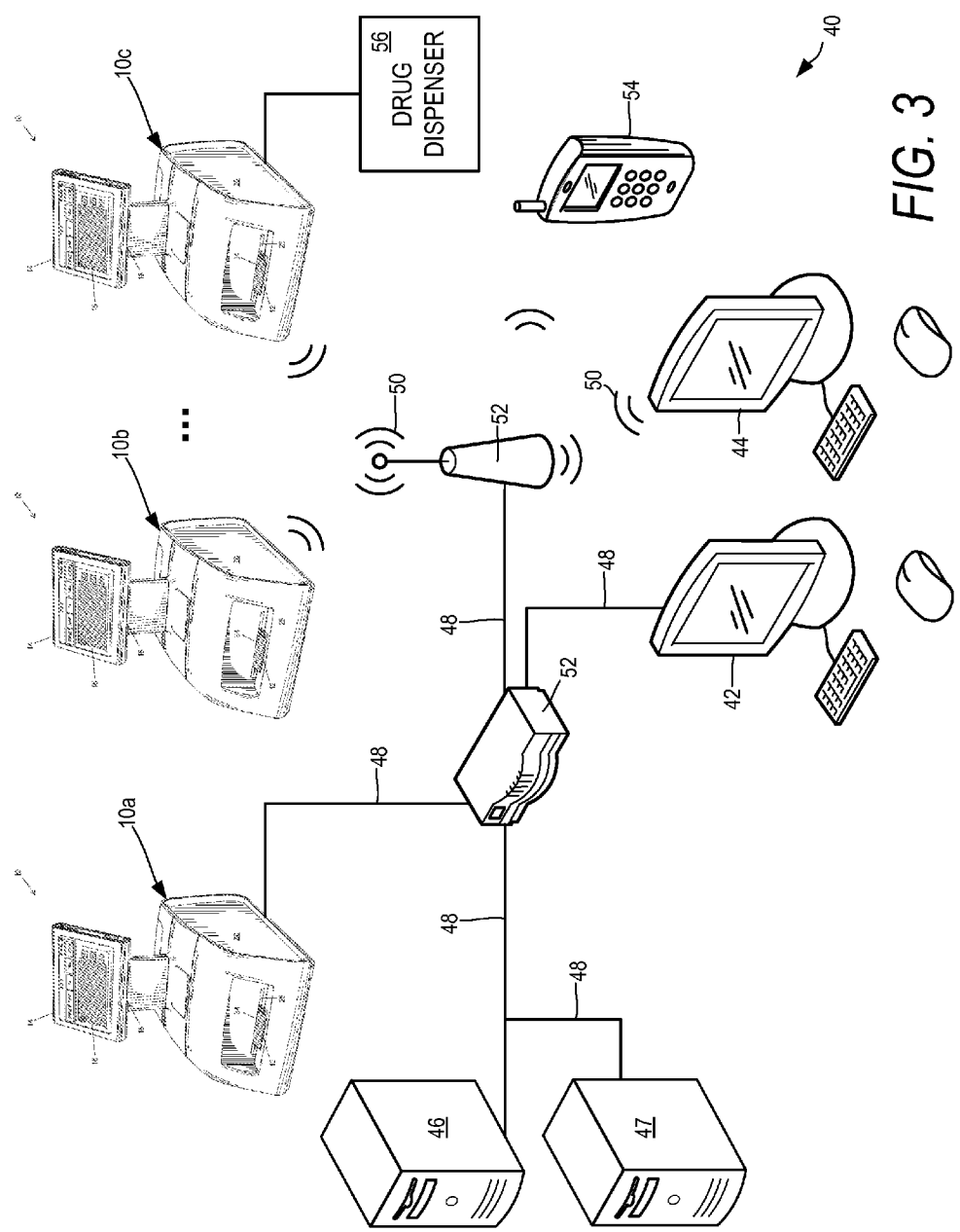
FIG. 3 shows an illustrative embodiment of a medical labeling network arrangement at a medical facility.

According to alternate embodiments, the configuration data 32 can be transmitted to, and received by the computer terminal over a computer network 40, an illustrative embodiment of which is shown in FIG. 3. The configuration data 32 can be assembled into a "package" to be transmitted, as a whole, by an administrative computer terminal such as a pharmacy computer terminal 42 described below, for example, over the communication network 40. Upon receiving the configuration package containing the configuration data 32, the computer terminal 10 can store the received configuration package in the memory 24, optionally replacing a previously received, or outdated, version of the configuration package to ensure only the current configuration package is actively in use by the computer terminal 10.

The packages referred to herein can be a single file, or a collection of individual files assembled into a single data unit, including a plurality of different operational parameters as the configuration data 32. For example, the configuration data 32 can include comma separated values (e.g., true/false/null; numerical values, etc. . . . ) of different operational parameters that govern operation of the computer terminal 10. Examples of the configuration data include, but are not limited to: time and location information, such as time, time zone and date to be established for the computer terminal 10; security information such as an identification of each authorized user of the computer terminal, login information for each authorized user, and the like; output information such as formatting codes governing the label content and appearance of labels to be generated by the computer terminal 10; hardware information such as printing resources available (e.g., identification of one or a plurality of: color inks available, size and orientation of label stock available, etc. . . . ) for printing labels; and other operational parameters that can be defined to govern, and optionally limit operation of the computer terminal 10.

In addition to the administrative instructions 30 and the configuration data 32, the memory 24 also stores an updatable formulary 36 containing a database of medicinal substances that can be identified by the computer terminal 10 and select information for each medicinal-substance entry in the database. The formulary 36 can optionally be stored, updated and deleted from the memory 24 by the introduction of a so-called smart drive comprising a USB compatible flash memory to the computer terminal 10. When the smart drive is introduced to the computer terminal 10, it loads and establishes the formulary 36 of the computer terminal 10. Illustrative examples of the select information that can be provided for the medicinal-substance entries includes, but is not limited to, an ID number such as a NDC code, UPC code, EAN code, or any other identifying data that can be used to relate a barcode or other computer-readable code to the medicinal-substance entries; a sound file that, when played, audibly announces the name of the medicinal substance identified in response to scanning a machine readable code; warning data; or any combination thereof.

Like the configuration data 32, the formulary 36 can optionally be assembled into a formulary package that can be transmitted from the pharmacy computer terminal 42 and received by the computer terminal 10 over the communication network 40, delivered via the USB drive, or any other desired transmission protocol. Thus, a formulary package received by the computer terminal 10 can optionally load an updated formulary 36 to replace, and purge from the memory 24, an existing formulary 36. Again, replacing the formulary 36 in the memory 24 as a whole by an updated edition of the formulary 36 can protect against reference to an outdated formulary 36. And for administrative purposes, replacing the formulary 36 in toto simplifies monitoring of versions distributed to a plurality of different computer terminals 10 included in the network 40. Each computer terminal 10 storing formulary X contains a database of known medicinal substances.

A network adaptor 38 is operatively connected to communicate with the processing component 22 for translating signals received by the computer terminal 10 over a network 40 at a medical facility, such as that illustrated in FIG. 3. The network adaptor 38 can be compatible with any type of network communication. For example, the network adaptor 38 can include a hardwired, 10Base-T, 100Base-T, or 1000Base-T Ethernet interface with an RJ-45 socket, a coaxial cable interface, a fiber-optic interface, any format of wireless communication interface such as an antenna compatible with any of the 802.11 standards established by the IEEE, or any combination thereof. Embodiments including wireless network adaptors 38 can employ any desired securing protocol such as WEP, WPA and WPA2, for example, and other suitable security protocol. For embodiments including a network adaptor 38 compatible to communicate over a plurality of different network communication channels, both a hard-wired communication portion of the network adaptor 38 and a wireless communication portion of the network adaptor 38 can optionally be concurrently active. Thus, the computer terminal 10 can optionally communicate via both the hard-wired and wireless portions of the network adaptor 38 concurrently.

As shown in FIG. 3, a plurality of the computer terminals, each referred to generally at 10 and separately at 10a, 10b, 10c, can be included in the network 40, which can be deployed at a healthcare facility. For example, each operating room in which surgical procedures take place may have one of the computer terminals 10 located therein. Other networks may include a computer terminal 10 in an examination room where procedures such as minimally invasive examinations of patients are conducted.

The network 40 also includes a pharmacy computer terminal 42 executing computer-executable instructions (referred to hereinafter as an administration tool or "AT") that, when executed, manage one or more, and optionally all of the computer terminals 10. Each computer terminal 10 to be managed by the AT can be optionally assigned a user-specified designation using the AT to distinguish the computer terminals from each other on the network 40, and to optionally provide the user with a brief description of each computer terminal 10. For example, a computer terminal 10 located in operating room #1 can be assigned the designation OR-1 to indicate its location. According to alternate embodiments, the user-specified name Cart-1 could be assigned to a computer terminal on mobile cart #1. An IT computer terminal 44 can also optionally be connected as part of the network 40 to execute the AT and allow technical personnel to manage technical aspects of the computer terminals 10, but optionally exclude from the permissions granted to technical personnel the ability to alter drug or other medical-related content stored by the computer terminals 10. The permissions granted to a user at the terminals 42, 44 can optionally be determined when the user logs in based on a username/password combination, a computer-readable identification, or any other identifying information. Thus, the terminals 42, 44 do not necessarily have to be dedicated solely for any particular purpose.

The pharmacy terminal 42 can be located in a pharmacy at a healthcare facility, where an inventory of controlled drugs and medicinal substances (hereinafter generally referred to as "drugs") is maintained. A pharmacist or a plurality of pharmacists maintain and administer a master drug database ("MDD") containing an identity, identification code (e.g., NDC) number, concentration and other pertinent information for drugs used by the pharmacy. Drugs are entered into the MDD by the pharmacist, and the terminals 42, 44, and optionally other terminals connected to the network 40 can restrict access to the MDD and prevent unauthorized individuals from entering or altering drug entries in the MDD, and optionally from accessing the MDD altogether. In other words, the pharmacist(s) registered and authorized to work at the health care facility and those they grant permission to access the MDD are the only individuals permitted to manipulate data in the MDD.

From the MDD, the pharmacist creates and manages one or more formularies to be stored in the memory 24 of one or more of the computer terminals 10 using the AT with the requisite pharmacist permission. The formulary can include a subset of the MDD, and the subset can optionally comprise drugs that are commonly used in the operating room or other locations at the healthcare facility where the computer terminal 10 is positioned. The same formulary can optionally be stored in the memory 24 of more than one computer terminal, and can optionally be customized to include drugs utilized during surgical procedures relating to a particular medical discipline. For example, the same formulary comprising drugs commonly used during cardiac surgical procedures may be stored in the memory 24 of computer terminals 10a, 10b, which are each located in a respective operating room dedicated for such procedures. Another, different formulary comprising drugs, optionally in appropriate doses, suitable to be administered to children can be stored in the memory 24 of a computer terminal 10 located in an operating room dedicated for pediatric surgical procedures. According to alternate embodiments, the formulary 36 stored in the memory 24 of a computer terminal 10 can be evaluated and updated, replaced or otherwise changed before each surgical procedure if the operating room where the computer terminal 10 is located is not dedicated for a particular type of surgical procedure. When a formulary update is needed to accommodate a specific type of procedure, a pharmacist's access can be required to update, replace or otherwise change the formulary in the computer terminals 10, and updating, replacing and changing the formulary in the memory 24 in each of the computer terminals 10 can be performed over the network as described in detail below.

In addition to a pharmacist's level of permission, there can be other permission levels limiting access to the computer terminals 10 to different users. For example, an anesthesiologist may be granted permission to use a computer terminal 10 to interrogate a barcode or other machine-readable code on a drug vial to extract the identity of the drug and print a label to be applied onto a syringe. The anesthesiologist can optionally also be granted permission to confirm that the interrogation of a barcode has returned the proper drug identification. However, the anesthesiologist may be prevented from editing the formulary stored in the memory 24 of the computer terminal 10.

Additionally, an IT professional can be granted permission to address any technical, computer hardware-and-software-related issues with the computer terminals 10 that are unrelated to the specific drug information of the MDD and/or formulary. For example, the IT professional may be granted permission to assign and/or change: an IP address of the computer terminals 10, a security protocol employed, and other computer-specific matters. However, some information related to the formulary such as the version and description of the formulary can be viewed by the IT professional to ensure that the proper computer terminal 10 has the correct formulary installation. This also applies to version and description information of the operating system, BIOS 28, configuration data 32 and administration instructions 30.

The network 40 in FIG. 3 also includes an email server 46 through which email is to be transmitted to individuals who perform tasks related to the computer terminals 10 at the healthcare facility. The email server 46, like the computer terminals 10, and optionally other resources of the network 40, can transmit signals to other network resources via hard-wired communication channels (represented by solid lines 48 in FIG. 3) such as CAT-5 Ethernet cable, via wireless communication channels (represented by arched, radiating signals 50), or a combination thereof. For example, email messages notifying individuals that a triggering event has occurred on one or more computer terminals 10 are transmitted from the email server 46 to one or more of the terminals 42, 44, a portable communication device 54 such as a personal digital assistant, cellular telephone, tablet or laptop computer, and the like. Additionally, the email server 46 can be configured to apply one or more rules that organize and deliver the information in more meaningful ways to the user. For example, a pharmacist may want notification of all problems with the formulary 36 (e.g., a "drug not found" notification) to be aggregated together and delivered to him at the start of his work shift and again 4 hours later. The email server 46 can be configured to transmit such notices in a single communication to the pharmacist at those times. Further, different pharmacists may prefer different notification procedures and different times at which such notifications are to be received, and the email server 46 can optionally be configured to satisfy the requests of each pharmacist individually. However, a group of IT technicians may want prompt notification of technical problems that prevent a computer terminal 10 from operating properly in a surgical suite. Again, the email server 46 can be configured to promptly transmit such notifications to the IT technicians substantially immediately upon detecting such technical problems.

Network resource allocation equipment 52 such as switches, routers, wireless access points, and the like can be included in the network 40 to share network resources and establish communication between the computer terminals 10 and the terminals 42, 44. Additionally, the computer terminals 10 can optionally serve as an expansion port to which other network resources such as the automated drug dispensing system 56, commonly referred to as a "smart cart", can be connected to the network to dispense and document the strength, quantity and type of drug according to a schedule or in response to the occurrence of a predetermined event. Additionally, since one of the functions of smart carts is to control the dispensing of drugs and one of the functions of computer terminal 10 is producing labels for containers such as syringes that are filled with drugs from the smart cart, there are benefits related to efficiency if the devices can share information. For example, a network connection between the smart cart and computer terminal 10 will allow user login information such as username and password entered on one device to be shared with the other device so a user is authenticated on both devices with a single login. Other benefits include being able to share information about drugs being used in a procedure between the devices so verification and reconciliation of drugs can be performed to ensure the proper medications are dispensed, labeled and tracked for improving the accuracy of patient records and accurate billing. As shown in FIG. 3, the automated drug dispensing system 56 is hard-wired to the computer terminal 10c, which is connected wirelessly to other network resources.

Before the computer terminals 10 are usable in a medical environment, the AT software can be installed on one or more of the terminals 42, 44 to be used by a pharmacist at a hospital or other health care facility to populate the MDD. The AT accepts drug information from various sources such as commercially available drug databases (e.g. Lexicomp) and allows the pharmacist to selectively add drugs to the MDD, which can be stored at network-accessible storage server or locally by the terminal 42, 44 running the AT. In simplest terms, the MDD is the set of drugs available to the hospital or other healthcare facility.

Once the MDD is populated with drug information, the pharmacist will use the AT to select a subset of drugs from the MDD to be added to the formulary that will be stored in the memory of one or more of the computer terminals 10, thereby enabling the computer terminals 10 to recognize the drugs in that formulary. The formulary managed using the AT running on one of the terminals 42, 44, as it pertains to the computer terminals 10, can be considered an official set of medications with associated information for preparing and labeling drug containers in accordance with a medical labeling standard. The "associated information" can include information for preparing the drug, which usually means diluting the drug when needed. It can also include information related to the color, patterns, graphics and textual information printed on the label for specific drugs to render those labels, once printed, compliant with the medical labeling standard. Other types of associated information can be files, data for implementing a computer-generated voice, references to files for audibly pronouncing the name of the drug and important drug related information such as the concentration value and concentration units, or any combination thereof. For example, in the case of Propofol 10 mg/ml, a single audio file, or more than one audio file or references to audio files can be combined together to audibly speak the drug name and concentration of the drug as "Propofol ten milligrams per milliliter". According to the present example, the drug name "Propofol" can be contained in one audible file while the concentration value "ten" is in another audible file and the concentration units "milligrams per milliliter" in a third audible file. These three audio files can be executed and played in sequence to allow the computer terminal to audibly broadcast "Propofol ten milligrams per milliliter" via the speaker 17 in response to the scanning of a barcode associated with the container that contains 10 mg/ml Propofol. Other audible information including information about errors such as "do not use drug", for example, can also be associated with a drug in the formulary using the AT. The "do not use drug" audible information can optionally be audibly output using the speaker 17 when a drug has been recalled and a pharmacist wants the computer terminals 10 to notify users not to use a drug that has been recalled, or is otherwise not suitable for use, for example. The computer terminal 10 can automatically assign some audible drug information by examination of the data related to the drug. For example, the concentration value 10 can be used to select the audible file or file reference that speaks the word "ten". The same applies to the concentration units. mg/ml can automatically be used to select the audible file or file reference corresponding to "milligrams per milliliter". Since the MDD can include information on many types of drugs used in the hospital including pills, capsules, ointments, patches, injectables, etc., the pharmacist can optionally select only the drugs from the MDD that are commonly used by anesthesiologists in the operating room (interchangeably referred to herein as the "OR") for a particular procedure or other points of care in the facility where drug containers are labeled prior to dispensing to patients. These are usually the injectable drugs. This subset of drugs can optionally be further narrowed into application-specific sets for pediatrics, etc. . . . .

Once the pharmacist selects the drugs for the formulary and assigns the associated information to each drug, the formulary package is created. As described above, this package is a single electronic file or a single collection of bundled electronic files containing all formulary information in a format suitable for delivery to the computer terminals 10 on which the formulary is to be stored. Assembling the formulary into a single package simplifies the transfer of information from the terminal operating the AT to the intended computer terminals 10. It also ensures that all information for that version of the formulary to be transferred to the computer terminals 10 is encapsulated in a single file so no information is lost or forgotten. The formulary package is then transmitted over the network 40 to the computer terminals 10 intended to receive the formulary package, as selected using the AT. According to alternate embodiments, the formulary package can optionally be stored on a USB flash drive and delivered to the computer terminals 10 by plugging the USB flash drive into the computer terminals 10 that are to receive the formulary package, which is then automatically installed. This makes the transfer an all-or-nothing proposition, meaning that the existing formulary on the computer terminals 10 is completely replaced by the formulary package being transferred. If the received formulary package is incomplete or corrupt, it will not be able to be installed on the computer terminals 10, and the user will be alerted to the installation failure.

In addition to delivering formulary packages, the computer terminals 10 accept other types of packages for configuration and software updates. Any of these packages can be delivered via USB drive or network. All packages are encoded with a digital signature to prevent the contents of the package being altered or corrupted. Additionally, the USB flash drive can optionally be required to possess a predetermined digital signature to ensure that only authorized USB flash drives can be plugged into the computer terminals 10 to install a formulary, configuration or software update package.

For example, the configuration package including the configuration data 32 is stored in the memory of the computer terminals 10 to control the behavior of those computer terminals 10 when preparing and labeling syringes. It is can be used to enable or disable features of the computer terminals 10 such as requiring verification that the drug information displayed on touch-screen display 14 matches the drug container scanned by scanner 18 before printing the label. Such verification can optionally be required only in response to the first time the code provided to the container is scanned, as described in U.S. patent application Ser. No. 13/357,669, which is incorporated in its entirety herein by reference.

Each formulary, configuration and software update package has an identifier string and version number. The identifier can provide human readable information that describes the contents of the package (e.g. Pediatric formulary). A unique version number is assigned to formularies and configuration packages automatically by the AT or from the vendor in the case of software update packages. The combination of the identifier string and version number makes each package easy to identify and track. The computer terminals 10 can display this information on the touch-screen display 14 or send it over the network 40 for remote monitoring. This is useful for tracking which systems have been updated and which system have not.

A plurality of different formularies can optionally be created and stored by different computer terminals 10 for different medical procedures. One formulary may contain drugs for general adult surgeries while another may contain different drugs or preparations (dilutions) for pediatric procedures. The AT allows multiple formularies to be created and managed from a single MDD. The user interface of the AT that controls the deployment of formulary packages over the network 40 allows the user to select a single computer terminal 10, as might be required for testing a new version of a formulary before wide-scale deployment, or a plurality or all of the computer terminals 10. In the case of multiple computer terminals 10, these can be manually selected or pre-assigned in groups so all computer terminals 10 in a group can receive the same formulary.

Each computer terminal 10 is designed to operate autonomously. Once it is has a formulary and configuration package installed, the computer terminals 10 can operate with or without a network connection to generate labels. This ensures the device will continue to work and not interfere with the medical procedure even if the network connection stops functioning. While the network is not functioning the computer terminals 10 will locally store information that needs to be transmitted for logging, record keeping, billing, and other purposes when the network connection is re-established.

When the computer terminals 10 are connected to the network 40 and the network connection is functioning properly, they can perform other functions in addition to receiving packages. For example, the computer terminals 10 can transmit information regarding the status of the: hardware (e.g., the printer 26 is low or out of a particular printing ink or toner, the printer is out of label stock), package information such as versions of packages installed, the user logged into each of the computer terminals 10 (if any), important events such as "drug not found" alert in response to scanning a barcode with the scanner 18, for example, which may indicate a drug is in the hospital that was not included in the formulary on that computer terminal 10 and may not be properly usable, etc. In such situations, an alert signal is transmitted by the afflicted computer terminal(s) 10 to the email server 46, and the email server 46 responds by composing the email or other message containing textual information corresponding to the alert signal and transmitting the email or other message to the intended recipient. The status information can optionally be transmitted by the computer terminals 10 automatically, not in response to receiving a status request, upon the occurrence of an event, periodically, when a status changes, or a combination thereof. According to an alternate embodiment, the AT running on the terminal 42 or 44 can be used to access the computer terminals 10 over the network 40 to determine the status of each computer terminal 10, the various components making up the computer terminals 10, or other information regarding the computer terminal 10. Thus, the AT running on the terminal 42 or 44 can be used to receive status report information autonomously transmitted by the computer terminals 10, and/or can be used to retrieve (or request transmittal of) the status report information from the computer terminals 10. The status report information can optionally be tabulated by the AT running on the terminal 42 or 44 and presented in a logical manner to the user, thereby allowing the user to readily identify any of the computer terminals 10 that are not operating as intended.

In another embodiment, event information that occurs on a computer terminal 10 can be shared with other computer terminals 10 on the network 40 either through the AT running on one or more of the terminals 42, 44, or the email server 46, or with a dedicated software program on the network 42, or directly with other computer terminals 10 on the network 42. Shared information can be used to optimize the workflow of the users by sharing events such as first time verification of a drug being used at a computer terminal 10 so other users will have the benefit of the drug verification and not have to perform the same verification procedure on each computer terminal 10.

At some point, the computer terminal 10 receives at least a portion of system information, which can be transmitted over the network 40 or otherwise delivered to the computer terminal 10. The system information can include, for example, any information concerning an operational characteristic of the computer terminal 10 itself. The configuration data 32 comprising parameters governing operation, and optionally the workflow of the computer terminal 10 can be received as part of the system information. Portions of the system information received necessary for independent operation of the computer terminal 10 are stored in the memory 24.

In addition to the configuration data 32, the system information can also optionally include information generated by the computer terminal 10 that is indicative of a status of the one or more portions of the computer terminal 10. Such self-generated system information can include status information indicating that a portion of the printer 26 or other portion of the computer terminal 10 requires the attention of an administrator such as the IT professional. Examples of such self-generated status information, any or all of which can be stored in the memory 24 and/or transmitted over the network 40 to be stored in a remotely-located (relative to the computer terminal 10) computer-accessible memory, include at least one of:

information indicative of a remaining capacity of toner and/or ink available to the printer 26 for printing label content (e.g., available ink/toner falls below a threshold level such as 25% of the original quantity available, toner or ink cartridge absent or completely exhausted, etc. . . . );

information indicative of a malfunction relating to the printer 26, or a portion thereof, that renders the printer inoperable to print label content;

information indicative of the number of labels on which the label content is to be printed available to the printer 26 falling below a threshold level (e.g., fewer than 25 labels or 25% of the original quantity remain, or the number of a particular color of label available has fallen below a threshold level, etc. . . . );

information indicating that receipt of a communication (e.g., one or more of the packages) via the network 40 was unexpectedly interrupted;

information indicative of a lack of communications between the computer terminal 10 over the network 40 for longer than a minimum, predetermined period of time;

information indicative of changes in the operational state of the computer terminal 10, such as time and/or date when the computer terminal 10 has been powered off, powered on, rendered inoperable (e.g., out of service, or out of service with logins allowed, etc. . . . );

information indicative of date, time, status (transferring, received but queued for installation, installation in progress, installation complete, installation and/or reception failed, etc. . . . ), or any combination thereof, of a package (e.g., formulary package, configuration package, etc. . . . ) received, at least in part, by the computer terminal 10; and any other information relating to an operational status of the computer terminal 10.

Embodiments of the computer terminal 10 can receive and/or generate drug information, which can be any information relating to events involving the computer terminal 10 and one or more drugs, and optionally store the drug information in the memory 24 and/or transmit the drug information over the network 40 to be stored in a remotely-located computer-accessible memory. The drug information can include information indicative of drug(s) identified by the processing component 22 in response to scanning codes with the scanner 18, along with other information related to the scanning of each such code. Illustrative examples of the drug information include, but are not limited to, at least one of:

an identity of a drug returned by the processing component 22 in response to scanning a computer-readable code with the scanner 18;

the concentration and/or quantity of the drug returned by the processing component 22 intended to be administered to the patient as input by the operator to the computer terminal 10 during the label generation process;

a time and/or date when each computer-readable code is read with the scanner 18;

the failure of the processing component 22 to identify a drug in a formulary corresponding to a computer-readable code read by the scanner 18;

the existence of a notation (e.g., drug obsolete, drug replaced, drug replaced by drug "XYZ" (where XYZ is the name of a replacement drug), drug not approved, etc. . . . ) in an entry of the formulary corresponding to a drug identified in response to scanning a computer-readable code with the scanner 18;

verification of a drug input to the computer terminal 10 the first time that drug is identified by the processing component 22 in response to scanning a computer-readable code with the scanner 18;

a lack of verification of a drug when that drug was first identified by the processing component 22 in response to scanning a computer-readable code with the scanner 18;

receipt of an override command input by an operator instructing the computer terminal 10 to proceed with preparing a label identifying a drug without verifying that the drug corresponds to the computer-readable code scanned by the scanner 18 when that drug is first identified by the processing component 22;

receipt of a command input by an operator to cause the computer terminal 10 to operate in a manner other than a permissible manner (i.e., in conflict with a permissible workflow stored in the memory 24);

errors encountered by the computer terminal 10 in response to scanning a computer-readable code with the scanner 18, such as: the inability to identify the type of computer readable code, the inability to interpret the computer-readable code, a failure to properly scan the code, an inability to generate the virtual label 16, input from the user indicating the presence of an error contained in a virtual label 16 presented by the display 14;

and any other information relating to the scanning of a computer-readable code by the scanner 18 and the drug associated with that code in the formulary, including the absence of such drug.

Information relating to dilutions is another example of drug information that can be logged by the computer terminal 10 and stored locally, at least temporarily before being transmitted to a remote archive over the communication network 40. If the operator inputs, via a soft key presented by the display 14 or via another input device, that a drug identified in response to scanning a barcode using the scanner 18 is to be diluted, a menu can be presented by the display 14. The menu can present the operator with at least one standard dilution, or a plurality of standard dilutions stored in the formulary that are selectable by the operator via the display 14 or other input device. A custom field can optionally be provided to allow the operator to enter a custom dilution that is not contained in the formulary or selectable using the computer terminal 10.

The permissible manner of operating the computer terminal 10 can optionally be defined by computer executable instructions stored in the memory 24, or any other computer-readable memory that is accessible by the computer terminal 10. The permissible manner of operation can optionally include soft limits, which result in the issuance of a notification to the user that the user is deviated from a recommended operating procedure. For instance, the computer terminal 10 can optionally establish a single-copy limit that allows only a single copy of each label to be printed via the printer 26. If a user attempts to input an instruction requesting more than one copy of the label 12 be printed, the computer terminal 10 can notify the operator that the permissible operating procedure allows only a single copy of the label 12 based on the scanned barcode to be printed. However, the computer terminal 10 can optionally allow the operator to override the single-copy limit and print a plurality of copies of the label. In response to receiving such an override instruction the computer terminal 10 can store the identity of the user in a log along with the drug information, the number of labels printed, and any other desired information described herein pertaining to the label printed.

The computer terminal 10 can optionally also receive and/or generate user information related to the user operating, and optionally logged in to the computer terminal 10. For example, when an operator logs into the computer terminal with a username and password combination, identification code, or other information uniquely identifying the operator, for example, the computer terminal 10 can generate a record identifying the user, along with the time and date of the operator's login. Further, a portion of the user information can optionally be combined with a portion of at least one of the drug information and the system information to relate the occurrence of an event involving the computer terminal 10 with a particular operator. Likewise, a record can be created to indicate when a user has logged out of the computer terminal 10.

For example, an operator can be presented with a request to input verification of a drug to the computer terminal 10 when that drug is first identified by the processing component 22 in response to scanning a computer-readable code with the scanner 18. The prompt for verification solicits independent, human verification of a computer-generated result, but does not necessarily require verification to be input as a condition of progressing with the process of preparing a label. Instead, the operator is also presented with an override option that, if selected, inputs a command instructing the computer terminal 10 to forego verifying the accuracy of the label content, such as the identity of the drug for example, to be printed on the label being generated. Under that scenario, the label content is printed to generate the label 12 without verification of the label content. Also, receiving the override command, the time and date on which the override command was received, the identity of the drug returned, and the name or other suitable information identifying the operator is assembled into a log entry in a running log stored in the memory 24 or a remotely-located computer-accessible memory connected to the network 24 where such events can be documented. Accordingly, in the event there is a dispute concerning usage of the drug that was labeled with the unverified label content, the log establishes a record document the label generation process. The record can include at least one of the system information, the drug information and the user information, and optionally a portion of two or more of the different types of information. In the present example, the identity of the drug as determined by the processing component 22 based on the code scanned with the scanner 18, the time and date on which the override command was input to the computer terminal 10, and the identity of the individual who input the override command can be included in the log entry corresponding to preparation of the label generated with the unverified label content.

Alternate embodiments of the computer terminal 10 can at least request, and optionally require, the operator to confirm that a label printed by the printer 26 is an accurate hardcopy reproduction of the virtual label 16. For instance, the computer terminal 10 can cause the virtual label 16 to be displayed subsequent to the printing of the label. Along with the virtual label 16, the display 14 can present soft keys the operator can physically touch to enter an instruction to the computer system 10 indicating that the printed label is, in fact, an accurate representation of the virtual label 16 being displayed. Likewise, another soft key can be selected by the operator to indicate that the printed label differs in some way from the virtual label 16, such as in formatting, content (e.g., incorrect drug identified, incorrect dosage, etc. . . . ). Although the feature can optionally be disabled by an administrator, if enabled, information pertaining to the operator and drug information relating to the printed label and/or the virtual label 16 can be stored in the log in response to being confirmed or objected to by the operator.

In addition to the information described above, the computer terminal 10 can optionally log "procedure Information" that is indicative of drug usage during a medical procedure. For instance, the procedure information can include a number of labels printed for a given medical procedure, optionally in combination with information identifying the drugs labeled and/or a quantity of the drugs expected to be administered. Such information can optionally be used in combination with a database of medicinal substances to allow for a determination of the value of the medicinal substances labeled, and believed to be consumed during a given medical procedure. For instance, the log entries for different medical procedures can indicate that Dr. A performs a hernia surgery and uses 6 drugs worth approximately $60, but Dr. B performs hernia surgery and uses 8 drugs worth $80. The identity of the patient is not necessarily required for such log entries because such information is not patient specific. Instead, procedure information logged can be utilized to document drug usage trends, which would suggest in the present example that the procedure performed by Dr. A will require fewer drugs, or at least incur a lower overall drug cost.

Each log entry in the running log maintained by the computer terminal 10 can optionally be locally stored by the memory 24 of that computer terminal 10. The locally stored entries can be transmitted occasionally, such as daily or following completion of each medical procedure during which the computer terminal 10 is utilized, for example, via the network 40 to a remotely-located computer-accessible memory, where they can be stored long term for documentation purposes. Events documented by SLS transmits over network to storage device. A cumulative database of all log entries recorded from a predetermined event, such as since the computer terminal 10 was put into service for example, can optionally be retrievable via a portable, computer-readable medium such as a USB flash drive inserted into a USB port provided to the computer terminal 10, for example. Further, any of the log entries described herein can optionally be generated by the computer terminal 10 automatically, without intervention from the human operator, in response to the occurrence of various triggering events, a list of which can be stored by the memory 24. According to alternate embodiments, one or more of the triggering events can be an operation performed by an operator using the computer terminal 10. Regardless of the nature of the triggering events, each log entry described herein can optionally be performed in a background environment, meaning that the log entries, when created, are not ordinarily visible on the display 14 during the label preparation process, and notice that a log entry has been created is not provided to the operator.

In addition to the above information, the computer terminal 10 can optionally also establish log entries that include patient-specific information. For such embodiments, the log entries containing patient specific information can be accessible to the computer terminal 10 where the patient-specific information was entered during, or in preparation for a medical procedure, or by a different network-connected computer terminal 10 that can receive such patient-specific information over the network 40 from the computer terminal 10 where the information was entered or another network-connected resource storing the patient-specific information. For example, in preparing a label for application to a syringe that is to contain a drug to be administered to a patient, the operator preparing the syringe can optionally enter a known allergen for the patient into the computer terminal 10. According to other embodiments, one or more known allergens to which the patient exhibits an allergic reaction can be received over the network 40 from a remotely-located source of patient information. The allergens received by the computer terminal 10 can be included in a log entry as patient-specific information related to information identifying that patient.

Once such a log entry has been created, the patient-specific information can be transmitted by the computer terminal 10 over the network 40 to a desired storage location, such as other computer terminals 10 on the network 40, or a computer-accessible memory on the network 40 dedicated to storing patient information such as an Electronic Medical Record (EMR) system 47 (FIG. 3). The EMR 47 can include a storage server that receives, stores and manages patient Personal Health Records from a variety of different sources throughout the healthcare facility and makes those records available to authorized users and equipment through the network 40. As related to computer terminals 10, patient information can be received by one or more of the computer terminals 10 over the network 40 from the EMR 47 of the healthcare facility using HL7 or another healthcare specific network protocol. Patient information such as patient name, ID, date of birth, sex, medical conditions, allergies, drug history and other relevant information are examples of the patient-specific information that can be stored by the EMR 47.

During a subsequent medical procedure involving a computer terminal 10 with access to previously-stored patient information, information such as last name, patient ID number, etc. . . . , can be entered by an operator into the computer terminal 10. Scanning a code with the scanner 18 to prepare a label for the drug associated with the code and identified by the processing component 22 can trigger a query of the patient-specific information for the identified patient executed by the processing component 22. Thus, if the patient-specific information includes an indication located by the query that the drug being prepared is a known allergen to which the patient is likely to exhibit an allergic reaction, the processing component 22 can initiate transmission of a warning (e.g., audible, visible via the display 14, etc. . . . ) to the operator.

In the above example, there may be instances where, in the operator's judgment, the risk of an allergic reaction to the drug is outweighed by the benefit of administering the drug to the patient. Perhaps the patient's allergic reaction to the drug is mild, or alternative drugs do not exist or, if they do exist, are not as therapeutically effective as the allergen drug. Similar to the override command described above, the computer terminal 10 can optionally present the operator with an option to continue preparing the label for the drug despite the warning issued by the computer terminal 10 in response to querying the patient-specific information and finding the allergy information related to that drug.

Figure 4A:
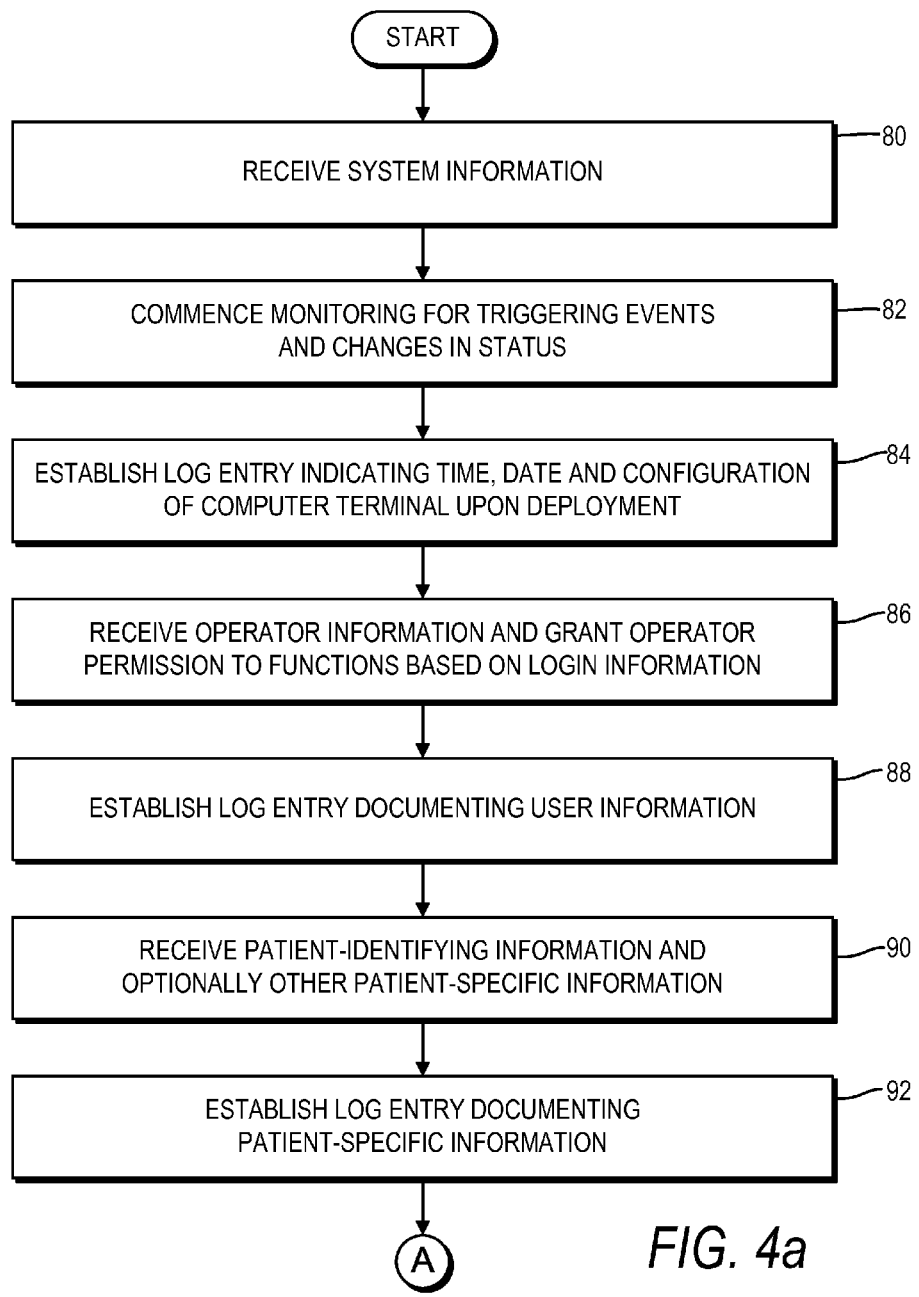
FIGS. 4*a*-4*c* show a flow diagram graphically representing a method of generating a label with the labeling apparatus appearing in FIG. 1.

Use of the computer terminal 10 to generate a label for identifying a drug in a container such as a syringe according to an illustrative embodiment is described with reference to FIGS. 4a-4c. As shown in FIG. 4a, the computer terminal 10 receives, at step 80, at least a portion of the system information including the configuration data 32, when the computer terminal 10 is deployed at the healthcare facility or prior to being deployed at a time when the computer terminal 10 is being setup for deployment at the healthcare facility. The configuration data 32 and other system information received establishes the workflow of the computer terminal 10, such as the steps and the order of steps to be performed to generate a label. Once deployed, the computer terminal 10 can begin to react to triggering events such as being powered on and/or receiving communications over the network 40, for example, and optionally monitor its status to generate log entries at step 82 documenting changes in the computer terminal's operational state in real time as they occur.

At step 84, a log entry can be established by the computer terminal 10, initiated by the processing component 22 executing computer-readable instructions, indicating a time and date on which the computer terminal 10 was powered on. In addition to the time and date, the log entry, or a separate log entry, can also optionally include other system information, such as a version and/or name of a formulary 32 stored in the memory 24, for example. The one or a plurality of log entries established and containing the system information can be stored in the memory 24 and/or transmitted over the network 40 to a desired storage location.

When a label is to be generated for use in a medical procedure, the computer terminal 10 receives login information such as an operator's username and password combination or other login information, for example, at step 86. The login information can be manually keyed or otherwise input by the operator, or the scanner 18 can be used to scan a computer-readable code provided to an ID badge issued by the healthcare facility to the operator. Regardless of the manner in which the login information is input, the computer terminal 10 can grant the operator limited access to operational features of the computer terminal 10 corresponding to the authorization level of the operator determined based on the login information received.

Since the operator's login constitutes an event involving the computer terminal 10, the creation of a log entry can be triggered in response to the operator's login at step 88. User Information indicative of the operator's identity and the time and date of the operator's login can be included in the log entry triggered in response to the operator logging in.

Once the operator has logged in, the computer terminal 10 is accessible to the operator for generating a label 12. At step 90, the computer terminal 10 can receive patient-identifying information uniquely identifying the patient that is the subject of a medical procedure during which the drug being labeled is to be administered. The patient-identifying information can include a portion of the patient's name, but can be an anonymous identifier such as a patient ID number, for example, that can be used to distinguish the patient from other patients but does not reveal the patient's identity by name or other personal information. In addition to the patient's identity, the computer terminal 10 can also optionally receive, at step 86, other patient-specific information, such as allergens to which the patient is sensitive and other known medical conditions input by the operator; received over the network 40 in response to a request for information corresponding to that patient transmitted by the computer terminal 10, the request for information including at least a portion of the patient-identifying information; or a combination thereof.

Again, as an event involving the computer terminal 10, the receipt of the patient-specific information triggers the creation of a log entry at step 92. The present log entry includes at least a portion of the patient-specific information allowing for identification of the patient upon reviewing the log entry, and a time and date on which the patient-specific information was received, along with information indicative of the operator who entered (i.e., was logged in at the time of entry) the patient-specific information.

Figure 4B:
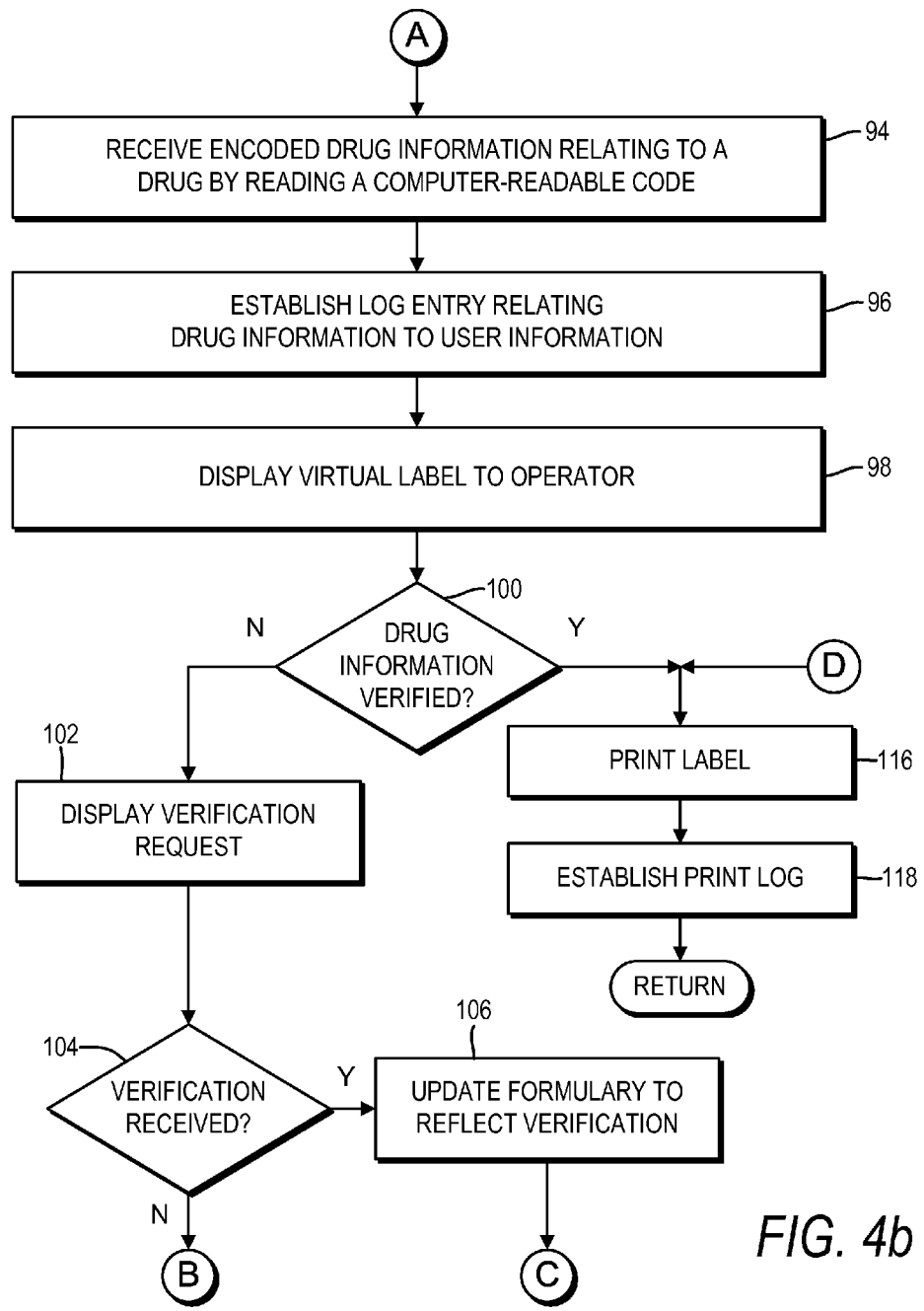

At step 94, shown in FIG. 4b, the computer terminal 10 scans a barcode or other computer-readable code using the scanner 18, and thereby receives a portion of the drug information. Using the encoded information (e.g., NDC number) obtained by scanning the barcode, the processing component 22 queries the formulary 32 for an entry with a matching NDC number, and returns at least a name of the drug and concentration of the drug associated with the same NDC number in the formulary 32. The time and date of the formulary query, the name and concentration of the drug returned by the query, and information indicative of the operator who scanned the barcode with the scanner 18 are included in a log established at step 96 in response to the triggering event of scanning the barcode.

If drug information corresponding to the code scanned can not be found by the computer terminal 10 in the formulary or other database, the computer terminal 10 creates a log entry indicating the barcode or other code scanned by the scanner 18 resulting in the "Drug Not Found" notice, and the operator who is logged in or otherwise identified as an operator at a time when the code was scanned. The computer terminal 10 can also optionally present to the operator an option to print a "blank" label, and provide an indication in the log entry when the operator prints a blank label. Although such a label is described as a "blank" label it can be printed or otherwise output by the computer terminal 10 to include at least a portion of the content that would be included on a label output by the printer 26 for a drug that is found in the formulary. For example, a desired color code, pattern, template can be selected for inclusion on the "blank" label. Information such as the operator's initials identifying the operator, the date and/or time the blank label was output, or any combination thereof can be included in the content of a blank label. A manually-entered drug identification can optionally be included in the content printed on a blank label, or a blank region can optionally be provided on the blank label to allow the operator to hand-write desired content. Any portion, or any combination of such information can be included in the log entry created for a request to produce a blank label entered into the computer terminal 10.

When the drug and concentration have been identified by the processing component 22, the virtual label 16 is presented to the operator by the display 14 at step 98 for verification purposes. At step 100, the processing component determines, based on information contained in the formulary 32 for the identified drug, whether the drug's identity, concentration and possibly other information returned from that entry in the formulary has previously been verified as accurate since being included in the formulary 32. If not, the display 14 also displays, at step 102, a request that the operator review the label content 34 shown as part of the virtual label 16, and input an indication whether the label content 34 is accurate or not. Such a request can optionally be accompanied by an option to override the requirement of user verification, allowing the label preparation process to proceed without verification, and possibly another option to terminate the label preparation process.

Figure 4C:
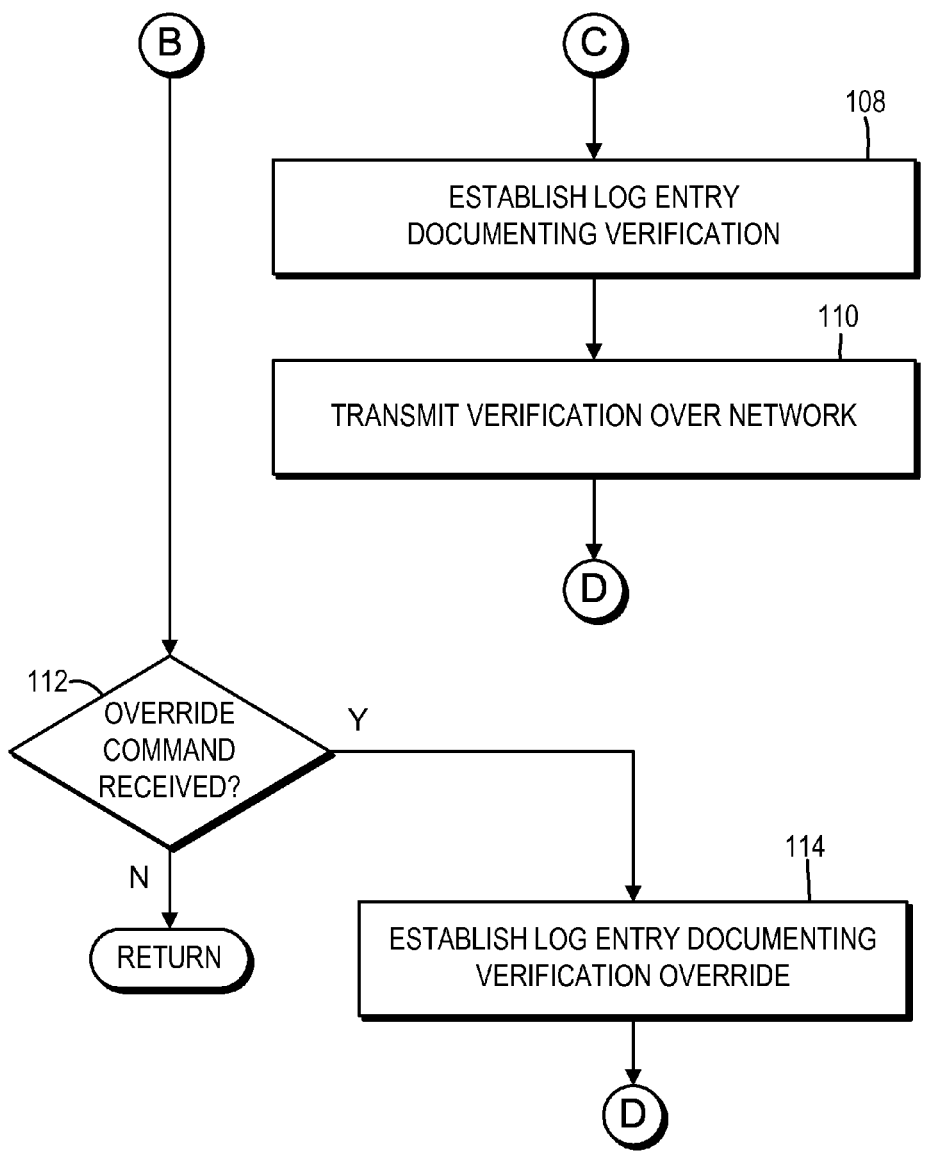

If it is determined at step 104 that, after reviewing the label content 34 the operator has confirmed the accuracy of the label content 34 and input the verification confirmation, the drug entry in the formulary 32 is edited at step 106 to indicate that that particular entry has been verified, and a log entry documenting a time and date of verification, the drug and its concentration, and information indicative of the operator is established at step 108 in FIG. 4c. Information indicating that the drug entry has been verified at step 104 (FIG. 4b) can optionally be transmitted at step 110 (FIG. 4c) over the network 40 to be shared with another network-connected device, which can include at least one of: another computer terminal 10, the pharmacy terminal 42, and any other networked device.

If at step 104 (FIG. 4b) verification is not received, then it is determined at step 112 (FIG. 4c) whether the operator has elected to terminate the label preparation process which, if selected, terminates the process of preparing a label 12. But if it is determined that the override command has been received by the computer terminal 10 at step 112, the computer terminal 10 generates a log entry, at step 114, including the time and date of the override command, the identification and concentration of the drug, and information indicative of the operator's identity, and proceeds with the label preparation process in progress. The label content 34 to be printed can optionally be modified in response to the absence of verification to include an indication that the drug information included in the label content 34 is unverified. Further, the computer terminal 10 can also optionally transmit an alert over the network 40 indicating that verification has been overridden or the process has been terminated at the verification stage to notify a pharmacist or other party authorized to edit the formulary 32 can investigate the drug entry.

If, at step 100 (FIG. 4b), the processing component 22 determines that, based on information contained in the formulary 32 for the identified drug, information corresponding to that entry of the formulary 32 has previously been verified, then presentation of the verification request can be omitted. Instead, the display 14 can display a soft key offering the operator the ability to terminate the label preparation process without printing the label 12, which terminates the process if selected, and a print option. Selection of the print option prints, at step 116, the label content 34 shown with the virtual label 16. A print log entry can also be established at step 118 to include the date and time the label 12 was printed; the drug's identity and concentration, and the quantity of the drug entered by the operator as the intended quantity of the drug to be administered to the patient; information indicative of the patient's identity, and information indicative of the operator's identity before concluding the label preparation process. As mentioned above, the virtual label 16 can be presented even after the label 12 is printed to allow the operator to compare the printed label 12 to the virtual label and indicate whether the content of the label 12 accurately reflects the content of the virtual label 16.

The contents of the label 12 printed can include a computer-readable code encoding at least a portion of the drug information pertaining to the drug and identified by scanning the code with the scanner 18 (e.g. drug identification, dosage information, concentration, expiration date and/or time, identification of person who prepared syringe and/or label, etc. . . . ) as disclosed in U.S. patent application Ser. No. 13/357,669, which is incorporated in its entirety herein by reference. Once the label has been printed at step 116, the scanner 18 can be used to scan the barcode printed on the label 12 at a time when the drug labeled by the label 12 is to be administered. In response to reading the barcode on the label 12, the computer terminal 10 creates a log entry including administration information such as a time the code on the label 12 is scanned, the operator who prepared the label 12 and/or scanned the code on the label 12, the identity of the drug and related information such as concentration and information indicating whether the drug has expired, or any combination thereof. The display 14 will also present the virtual label 16 corresponding to the code printed on the label 12 to allow the operator to visually compare the contents of the label 12 with the contents of the virtual label 16 and confirm the consistency of the compared information. The computer terminal 10 can also warn the operator if the drug prepare has expired. Additionally, the computer terminal 10 can also detect, from scanning the code on the label 12 with the scanner 18, whether a different computer terminal 10 was used to prepare that label 12. An indication whether a different computer terminal 10, other than the computer terminal 10 used to scan the code printed on the label 12, was used to prepare that label can be included in a log entry, and optionally broadcast a warning to the operator when such a condition has been detected. Such a warning can be useful where the computer terminals 10 are each dedicated for use at a given location (e.g., given operating room) in a medical facility. The warning would indicate when a label prepared for a drug in one operating room is scanned when the drug labeled is to be administered at a different location, which my violate an acceptable operating procedure established at the medical facility.

The log generated by the computer terminal 10 including entries relating to at least one of the system information, user information, drug information and patient information can be stored in the memory 24, at least until the log can be transmitted to an ultimate storage device over the network 40. The log can optionally be transmitted over the network 40 according to a predetermined transmission, such as at the end of a medical procedure when the operator logs off of the computer terminal 10, daily, weekly, etc. . . . , at which time the log in the memory 24 can designated as being available to be written over. The log can also optionally be retrieved locally, at the computer terminal 10, and stored on a portable computer-readable medium (e.g., USB flash drive) introduced to the computer terminal 10.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A labeling apparatus that generates a label for labeling a drug container, the labeling apparatus comprising:
   a code reader that interrogates a computer-readable code;
   a non-transitory, local computer-readable memory that stores a drug formulary comprising a plurality of drug entries;
   a processing component configured to identify, from the formulary, a specific drug that corresponds to the computer-readable code read by the code reader, and further configured to create log entries in a historical record documenting usage of the labeling apparatus in a non-transitory computer memory accessible to the labeling apparatus in response to triggering events, wherein the log entries comprise at least one of:
      system information, user information, drug information, and patient information; and
   a printer for printing label content identifying the specific drug onto a label that is to be applied to the drug container.

2. The labeling apparatus of claim 1, wherein the non-transitory, local computer-readable memory stores a configuration package comprising operational parameters of the labeling apparatus, and the formulary package and the configuration package are each updatable in whole.

3. The labeling apparatus of claim 1, wherein the printer is integrally formed as part of a chassis that supports the code reader and prints label content in a manner that is compliant with a medical labeling standard.

4. The labeling apparatus of claim 1, wherein the log entries created by the processing component comprises a log entry documenting a deviation from an accepted workflow stored in the non-transitory, local computer-readable memory, and the log entry documenting the deviation comprises information indicative of an identity of an operator utilizing the labeling apparatus to prepare the label and information indicative of the label generated by the labeling apparatus.

5. The labeling apparatus of claim 4, wherein the information indicative of the label generated by the labeling apparatus comprises: a name of the specific drug, a concentration of the specific drug, and information about a nature of the deviation from the accepted workflow.

6. The labeling apparatus of claim 1, wherein the log entries comprise at least one log entry comprising a combination of two or more of the system information, the user information, the drug information, and the patient information.

7. The labeling apparatus of claim 1, wherein at least one of the log entries is created automatically by the labeling apparatus in response to a triggering event, without intervention from an operator.

8. The labeling apparatus of claim 1, wherein at least one of the log entries comprises patient information that includes patient-specific information entered by an operator and received by the labeling apparatus, the patient-specific information comprising information about a medical condition of the patient.

9. The labeling apparatus of claim 8, wherein the patient-specific information is stored by at least one of the non-transitory, local computer-readable memory and a computer-accessible memory accessible over the network, and the processing component compares the patient-specific information to the specific drug to determine whether the medical condition renders administration of the specific drug to the patient problematic.

10. The labeling apparatus of claim 1 further comprising a network component compatible with a communication protocol designate for use in a medical setting that transmits the log entries to a destination storage location over a communication network.

11. The labeling apparatus of claim 10, wherein the network component transmits the log entries to the destination storage location at a predetermined transmission time.

12. The labeling apparatus of claim 11, wherein the predetermined transmission time comprises at least one of: a time when an operator logs off of the labeling apparatus, a specific time on a particular day, and a periodical transmission time.

* * * * *